United States Patent
Merz et al.

(10) Patent No.: US 9,770,235 B2
(45) Date of Patent: Sep. 26, 2017

(54) ASSEMBLY METHOD FOR A MICROSURGICAL INSTRUMENT, AND PIVOTABLE RETRACTOR

(71) Applicant: KARL STORZ GMBH & CO. KG, Tuttlingen (DE)

(72) Inventors: Robin Merz, Furtwangen (DE); Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 95 days.

(21) Appl. No.: 14/615,155

(22) Filed: Feb. 5, 2015

(65) Prior Publication Data
US 2015/0223796 A1    Aug. 13, 2015

(30) Foreign Application Priority Data
Feb. 10, 2014    (DE) .................. 10 2014 101 601

(51) Int. Cl.
*A61B 1/32*    (2006.01)
*A61B 17/02*    (2006.01)
(Continued)

(52) U.S. Cl.
CPC .......... *A61B 17/0218* (2013.01); *A61B 17/29* (2013.01); *A61B 2017/0046* (2013.01);
(Continued)

(58) Field of Classification Search
CPC ..... A61B 17/02; A61B 17/0218; A61B 17/29; A61B 17/00234; A61B 1/32;
(Continued)

(56) References Cited

U.S. PATENT DOCUMENTS

| | | | |
|---|---|---|---|
| 6,874,828 B2 * | 4/2005 | Roatis | E05B 17/0029 292/199 |
| 7,296,804 B2 * | 11/2007 | Lechot | A61B 17/1666 279/75 |
| 9,480,466 B2 * | 11/2016 | Van De Weghe | A61B 17/00234 |
| 2012/0239010 A1 * | 9/2012 | Shelton, IV | A61B 17/1155 606/1 |

(Continued)

FOREIGN PATENT DOCUMENTS

| | | |
|---|---|---|
| DE | 19707373 C1 | 2/1998 |
| DE | 19722062 A1 | 12/1998 |

(Continued)

*Primary Examiner* — Jacqueline Johanas
*Assistant Examiner* — Tessa Matthews
(74) *Attorney, Agent, or Firm* — Whitmyer IP Group LLC

(57) ABSTRACT

The present invention discloses an assembly method for a microsurgical instrument, which has a proximal handle mechanically connected to a hollow shaft. The shaft is coupled releasably to a tool head via a bayonet connection. The handle has at least one actuation device, which is operatively coupled to an actuation rod that is guided in the shaft. The bayonet connection has two bayonet elements with respective longitudinal slits which are aligned in a locked state of the bayonet connection, wherein at least one longitudinally movable cam is guided axially in the longitudinal slits. The actuation rod is inserted with its proximal end portion into the handle and has a flattened part, which is engaged by a clamping block arranged on the handle in a fixed position with respect to the longitudinal axis. Moreover, a pivotable retractor is disclosed.

6 Claims, 8 Drawing Sheets

(51) Int. Cl.
*A61B 17/29* (2006.01)
*A61B 17/00* (2006.01)

(52) U.S. Cl.
CPC ............ *A61B 2017/00477* (2013.01); *A61B 2017/00526* (2013.01); *A61B 2017/2902* (2013.01); *A61B 2017/2927* (2013.01); *A61B 2017/2931* (2013.01); *Y10T 29/49826* (2015.01)

(58) Field of Classification Search
CPC .. A61B 2017/0046; A61B 2017/00477; A61B 2017/00526; A61B 2017/2902; A61B 2017/2927; A61B 2017/2931; Y10T 29/49826; A61M 29/00
See application file for complete search history.

(56) References Cited

U.S. PATENT DOCUMENTS

| | | | | |
|---|---|---|---|---|
| 2013/0310812 A1* | 11/2013 | Stefan | .................... | A61B 17/29 606/1 |
| 2013/0310814 A1* | 11/2013 | Bacher | .................. | A61B 17/00 606/1 |
| 2015/0223797 A1* | 8/2015 | Merz | ................. | A61B 17/0218 600/216 |

FOREIGN PATENT DOCUMENTS

| | | |
|---|---|---|
| DE | 19920869 A1 | 12/2000 |
| DE | 102006038516 A1 | 2/2008 |
| DE | 102012007645 A1 | 10/2013 |

\* cited by examiner

ASSEMBLY METHOD FOR A MICROSURGICAL INSTRUMENT, AND PIVOTABLE RETRACTOR

FIELD OF THE INVENTION

The present invention relates to an assembly method for a microsurgical instrument, and a pivotable retractor.

BACKGROUND OF THE INVENTION

Microsurgical instruments, for example retractors, are often designed to be able to be dismantled, so as to be able to be more easily cleaned. The shaft, the handle and the retraction structure, or another working structure, can be separable from one another. It is known for the connection between the shaft and the retraction structure, or the other working structure, for example a tool head, to be produced by a releasable coupling device such as a bayonet catch.

DE 10 2006 038 516 A1 discloses a tubular shaft instrument with an actuation rod which is guided in a shaft, and of which the proximal end can be connected to an actuation element, and of which the distal end is coupled to the tool head for actuating the tool.

A sleeve lies on the tool head and is releasably coupled to the hollow shaft via a pin-and-slot connection with a curved guide track.

Although pin-and-slot connections or bayonet connections have the advantage of being able to be operated intuitively and quickly, they tend to come apart automatically under a torsional load, which poses a safety risk especially in the case of tool heads of considerable weight or tool heads with considerable radial projection, such as a retraction structure. Attempts were therefore made to seek solutions that would make accidental release of the bayonet connections more difficult.

A bayonet connection of this kind, provided for connecting two tubular instrument parts, is disclosed in DE 197 07 373 C1. There, on a distal half of the instrument, a bayonet sleeve is provided which has an L-shaped slit, wherein a bayonet insert, with engagement lugs protruding radially and along the longitudinal axis, is inserted into the bayonet sleeve. Arranged distally "behind" the bayonet sleeve is a locking piece which is pressed in the proximal direction by a spring and, on its end face, has a recess whose shape corresponds to the lugs of the bayonet insert. When the bayonet insert is located in its rotation-locking position, the lugs engage in the recess and the locking piece springs back, as a result of which further rotation of the bayonet insert is suppressed. While the solution proposed there makes rotation more difficult, it does not entirely prevent it, since, if the torque on the shaft is high enough, the locking piece can be moved counter to the spring load, as a result of which the engagement with the recess is canceled.

Further modified bayonet connections were therefore developed that were intended to more reliably suppress any accidental rotation.

Thus, DE 10 2012 007645 relates to a joint device for a medical instrument in which a handle, by way of a shaft, is coupled to a joint by means of a bayonet. An actuation rod and an inner shaft, which are provided for the operation of tool functions, are provided in the shaft. The (outer) shaft is connected to a joint body via the bayonet connection. For this purpose, a sleeve, with radially protruding claws at its proximal end, is arranged on the proximal end of the joint. The sleeve has a longitudinal axial slit through which a radially protruding cam, secured in a fixed position on the inner shaft, emerges. This cam has a greater length and extends radially farther than the sleeve is thick. The cam can be brought together with the inner shaft to a distal end position in which it is received on the joint body in a corresponding niche of a flange of the sleeve. At its distal end, the (outer) shaft has an L-shaped slit which is pulled over the sleeve of the joint body for the coupling, wherein the claws are brought into engagement with the slit.

The longitudinal axial slit portions and the niche of the flange, in which the cam is received, are aligned in the locking position of the bayonet, such that the cam can be moved out of the niche in the proximal direction into the longitudinal axial slit portions, as a result of which an anti-rotation means is achieved. There, however, the anti-rotation means can become effective only when the cam is moved out of the niche and is in engagement with the two longitudinal axial slit portions.

SUMMARY OF THE INVENTION

Proceeding from this prior art, the object of the present invention is to ensure that a microsurgical instrument that works with a bayonet catch is able to be assembled such that, in each operating state of the instrument, an effective anti-rotation means is provided for the bayonet connection.

This object is achieved by the assembly method for a microsurgical instrument with the features of the claimed invention.

There is the further object of making available a pivotable retractor that is distinguished by increased operating safety and intuitive control.

This object is achieved by a pivotable retractor with the features of the claimed invention.

Developments of the method and of the device are described by the respective dependent claims.

The assembly method according to the invention is provided for assembling a microsurgical instrument which has a proximal handle mechanically connected to a hollow shaft. The shaft is coupled releasably to a tool head via a bayonet connection, and the handle has one or more actuation devices operatively coupled to an actuation rod that is guided in the shaft. The bayonet connection has two bayonet elements with respective longitudinal slits which are aligned in a locked state of the bayonet connection. A common longitudinally movable cam is guided in the longitudinal slits. The actuation rod is inserted with its proximal end portion into the handle and has one or more flattened parts, which is (are) engaged by at least one clamping block arranged on the handle in a fixed position with respect to the longitudinal axis.

The method comprises the following steps:
a) making available the handle, the hollow shaft and the tool head, with the actuation rod operatively coupled thereon,
b) pushing the shaft, with one of the bayonet elements at the front, over the actuation rod and bringing the bayonet element of the shaft into engagement with the other bayonet element,
c) rotating the shaft and the tool head relative to each other until the bayonet connection is in the locked state, thereby also aligning the longitudinal slits of the bayonet elements,
d) inserting the proximal end portion of the actuation rod into the handle, thereby engaging the flattened part of the actuation rod with the clamping block of the handle and securing the actuation rod against rotation relative to the handle, e) mechanically connecting the handle to the shaft, f) moving the cam into the longitudinal slits and forming an anti-rotation means near the tool.

In contrast to known microsurgical instruments that have a similar anti-rotation means near the tool, the inventive combination of the anti-rotation means near the tool along with the engagement of the clamping blocks of the handle on the flattened part of the actuation rod creates a redundant second anti-rotation means, which is already active when the anti-rotation means near the tool is still not active. It is thus possible to effectively prevent the bayonet connection from opening shortly after closure, without any action on the part of the user being needed to activate the anti-rotation means "near the handle". The anti-rotation means "near the handle" is achieved solely by bringing the clamping block of the handle into engagement with the flattened part of the actuation rod, which takes place as it were "automatically" upon inserting the actuation rod into the handle. To ensure that the cam is able to engage with a locking action in both longitudinal grooves, i.e. the longitudinal groove of the two bayonet elements, the cam has to pass at least partially through the thickness of both bayonet elements. It is also possible to use more than one cam, in which case each cam can be guided in its own longitudinal groove.

Moreover, the cam can be connected to the actuation rod for conjoint movement therewith, in which case, in step f), the actuation device of the handle is actuated and, in this way, the actuation rod is moved along the longitudinal axis, and the cam is necessarily carried along with it.

In this way, the cam can be moved in the customary movement paths using the handle, without the cam having to be moved directly by hand for this purpose, which thereby provides improved ergonomics.

Moreover, the longitudinal slits of the bayonet elements and one or more engagement bodies of the bayonet connection can be at an angular offset in a release state of the bayonet connection, wherein, in step b), a distal end of a bayonet element assigned to the shaft is brought to bear on the cam, and the cam is carried along in the movement of the shaft.

By means of the angular offset of the one or more engagement bodies and of the longitudinal slits with respect to the longitudinal axis, it is possible to ensure that the two longitudinal slits of the bayonet elements are in alignment in the locked state. Moreover, when the shaft is pushed over, the cam can be carried along by a portion of the distal end of the bayonet element assigned to the shaft, while the one or more engagement bodies are inserted into the one or more longitudinal slits.

Finally, at a proximal end of the tool head, an attachment portion can be present which has a niche that corresponds to a size and position of the cam. Before step c), it is possible to carry out step b'), i.e. moving the cam to a distal end position of movement, there receiving the cam in the niche and thereby releasing a degree of freedom of rotation of the bayonet elements. The niche in this case has to be at least as long as the cam, such that, when the cam is received in the niche, the two bayonet elements can be pushed one into the other and rotated.

The tool head can be a ring retractor, which can also be pivotable. An effective anti-rotation means for the bayonet connection is important specifically in the case of pivotable ring retractors, since these have a comparatively long and heavy retraction structure, as a result of which a comparatively high torque is exerted on the bayonet connection by the inherent weight alone, which torque is even higher in the pivoted state than in the extended state.

If the microsurgical instrument moreover has a sleeve which is connected in a rotationally fixed manner to the handle, in which the actuation rod is guided movably along the longitudinal axis, and the sleeve has, in its wall, at least one opening in which the clamping block is fitted, it is possible, before step d), to carry out step c'): pushing the actuation rod into the sleeve until the flattened part is present at a longitudinal axis position of the clamping block, thereafter turning the actuation rod until the clamping block bears on the flattened part, and, together with the actuation rod, inserting the sleeve into the handle.

A receiving bore of the handle, into which bore the sleeve is inserted, corresponds with minimal play to the sleeve diameter at the longitudinal axis position where the clamping block lies, as a result of which the clamping block is not pressed out of the opening, even when the actuation rod is subjected to a torque, but instead provides a form-fit lock against rotation of the actuation rod.

The retractor according to the invention has a proximal handle connected to a hollow shaft, which shaft is coupled releasably to a retraction structure via a bayonet connection. The handle has one or more actuation devices operatively coupled to an actuation rod that is guided in the hollow shaft and operatively coupled to a joint of the retraction structure. A first cylindrical bayonet element is present in a rotationally fixed position in a distal end portion of the shaft and has a longitudinal axial slit portion open in the distal direction. A second cylindrical bayonet element, present in a rotationally fixed position in a proximal attachment portion of the retraction structure, engages with the first bayonet element and has a longitudinal slit which, in a locked state of the bayonet connection, is aligned with the longitudinal axial slit portion of the first bayonet element. A cam is guided movably along the longitudinal axis in the longitudinal axial slit portion of the first bayonet element and in the longitudinal slit of the second bayonet element, said cam being arranged in a fixed position on the actuation rod. The actuation rod has one or more flattened parts in its proximal end portion. The handle has one or more clamping blocks arranged in a fixed position on the handle and engaging in a locking action with the flattened part of the actuation rod.

Retraction structures are known. They have a plurality of articulated members that can be closed to form a ring, wherein the member at the free distal end of the retraction structure has a head with which it can be closed to form the ring, which can placed under an organ that is to be retracted. Pivot mechanisms are also known. These have a stationary part, with which they are connected to the shaft, and a second part which can be pivoted relative thereto and carries the members. To actuate the pivoting, the actuation rod of the retractor is joined to a transmission arm or linking rod, which in turn is connected at the distal end to an eccentric force exertion point of the pivotable second part.

The actuation rod can have exactly one flattened part, which can be a portion with a cross section in the shape of a segment of a circle, two opposite flattened parts, or flattened parts distributed polygonally about the circumference of the actuation rod, arranged for example in the shape of a regular hexagon.

According to the invention, two anti-rotation means operatively separate from each other are achieved, which permit reliable protection against accidental opening of the bayonet connection in each operating state of the retractor. The anti-rotation means near the tool, obtained through the engagement of the cam in the longitudinal slits, takes up a torque that is exerted by the inherent weight of the retraction structure and/or by external loading by an organ, near to where the force is introduced, while the anti-rotation means obtained by the one or more clamping blocks provides an additional anti-rotation means in the event that the anti-rotation means near the tool is inactive, which is the case when the cam has not yet been moved into the longitudinal slits of the two bayonet elements. The first and/or the second bayonet element can be produced as an integral component of the shaft and/or of the proximal end of the retraction structure or, during the manufacture of the retractor, can be produced first as a separate component and joined to a shaft blank or a retraction structure blank.

In a further embodiment, the actuation rod can be movable along the longitudinal axis in a predetermined work area, and the flattened part of the actuation rod can be at least as long as the predetermined work area. This ensures that the actuation rod can be moved unimpeded over its full work area. However, for coupling/uncoupling the actuation rod to/from the anti-rotation means obtained by the one or more clamping blocks on the handle, the clamping blocks can slide beyond the flattened part, as a result of which the locking engagement can be overcome.

In a further embodiment, the actuation rod can have a recess extending at least along a circumferential portion. The cam can have a C-shaped foot, which corresponds to the dimensions of the recess, wherein the cam is suspended with the foot in the recess of the actuation rod.

The cam can be held in the recess simply with a form fit or can additionally be held by another connecting method, for example welded or adhesively bonded to the actuation rod. However, said connecting methods do not limit the invention, and, indeed, other ways of securing the cam are possible.

In yet another embodiment, the second bayonet element can have, at its proximal end, at least one claw or a plurality of claws. These can be, but do not have to be, arranged at uniform angular intervals. The one or more claws extend radially outward and in each case form an engagement body that engages with the first bayonet element.

If a plurality of claws are used, an associated L-shaped slit is provided in the other bayonet element for each of the claws. With two or more claws, the transmissible torque of the bayonet connection can be increased, and, with comparatively wide manufacturing tolerances, it is possible to reduce the tendency to tilting.

Alternatively or in addition, the one or more claws, in the locked state of the bayonet connection, can be angularly offset with respect to the longitudinal axial slit portion of the first bayonet element. In this way, it is possible to ensure that the two longitudinal slits of the bayonet elements are in alignment in the locked state and also that, when the shaft is pushed over, the cam can be carried along by the free distal end of the bayonet element assigned to the shaft, while the one or more engagement bodies are inserted into the one or more slits. When coupling the shaft, the person operating the retractor does not have to pay attention to which position the cam is located in; the cam is moved along by the distal end of the shaft during the coupling procedure.

According to a further embodiment, the retraction structure can have a cylindrical attachment portion to which the second bayonet element is connected. A proximal end portion of the attachment portion has a niche which corresponds to a size and position of the cam, wherein the cam can be received in the niche in its distal end position of movement.

The cylindrical attachment portion of the retraction structure can also be designated as a stationary part, since it is connected to the shaft and in particular also has the joint for pivoting the distal, movable part of the retraction structure.

The niche in the proximal end portion of the attachment portion makes available a receiving space for the cam, in which the latter can be received temporarily for the assembly of the bayonet connection, so as not to impede the rotation of the two bayonet elements. In this position, it can be moved in the distal direction by a corresponding movement of the actuation rod. On the handle, provision can be made that the "additional" path of movement into the niche can be achieved only after a lock has been overcome, so as to prevent this position from being reached inadvertently. This position lies outside the normal work area of the actuation rod and is needed only for the assembly/disassembly.

In addition, the second bayonet element can have, at its distal end, a collar with a circumferential interruption. The width of the interruption can correspond to the width of the cam, wherein the interruption forms a continuation of the longitudinal slit of the second bayonet element, and the niche is formed, for example, by the interruption of the collar. Alternatively or in addition, the cylindrical attachment portion of the retraction structure can have, at its proximal end, a radially outer lug, which extends in the proximal direction along the longitudinal axis and engages in the interruption of the collar.

By means of the engagement of the lug in the interruption, it is possible, during manufacture, to achieve a defined angle of the bayonet elements assigned to the retraction structure and of the attachment portion of the retraction structure, which makes it easier to position the bayonet element correctly for a subsequent welding procedure or for connection by means of other joining techniques. In addition, however, provision can also be made that the lug engages with a form fit in the interruption even during the operation of the retractor, without the bayonet element having to be welded; here, for example, the bayonet element can be assembled using latching means or similar connecting elements. The width and longitudinal axial orientation of the interruption advantageously corresponds to the width of the longitudinal slit of the bayonet element assigned to the retraction structure; the longitudinal slit extends further as it were in the distal direction right through the collar.

Moreover, a sleeve can be connected in a rotationally fixed manner to the handle, in which the actuation rod is guided movably along the longitudinal axis. The sleeve can in particular have, in its wall, one or more openings in which the one or more clamping blocks are fitted. The sleeve can be surrounded by a pressing device, for example a spring ring, an elastomer ring and/or an elastic hose section, which is designed to apply a radially inward pressing force to the clamping block.

The outer contour of the clamping block can advantageously be shaped such that, in the inserted state, it forms a "continuation" of the cross section of the main body with a gentle transition, such that, even with the clamping block inserted, the sleeve can be inserted into a corresponding receiving bore of the handle. The sleeve can have a round or angled outer cross section, which can be advantageous for securing the sleeve with a form fit against rotation with respect to the handle. During disassembly of the retractor, the sleeve is intended to be removed from the handle together with the actuation rod, since the engagement of the clamping block in the flattened part cannot be overcome in the inserted state.

The radial fit of the clamping block in the receiving bore of the handle is advantageously so tight that, even upon rotation of the actuation rod, the clamping block is pressed away only inappreciably in the radial direction. In addition to the elements mentioned by way of example, the pressing device can also take other forms, for example a band-shaped tensioning element.

According to yet another embodiment, the sleeve can have, in a proximal end portion, one or more grooves in which at least one corresponding engagement means of the handle engages. Alternatively or in addition, the sleeve can have, in a distal end portion, a coupling device which is releasably connected to a proximal end of the shaft for conjoint rotation and movement therewith. The coupling device can have, for example, a plurality of circumferentially arranged longitudinal grooves, each of them in engagement with an inwardly protruding tongue of a coupling piece, which is arranged on a proximal end of the shaft.

The circumferential groove in the proximal end portion of the sleeve serves to couple the sleeve to the handle for conjoint movement therewith, wherein corresponding engagement means of the handle, for example radially extending pins or tongues, are brought into engagement with the circumferential groove. The longitudinal grooves at the distal end of the sleeve, together with corresponding engagement ribs of the coupling piece of the shaft, are intended to connect sleeve and shaft securely in terms of rotation. In one embodiment, the longitudinal grooves can be arranged, for example, at regular angular intervals. The coupling piece of the shaft is a kind of head or connection adapter which permits convenient handling of the shaft and has sufficient stiffness for coupling to the grooves.

Finally, the longitudinal grooves of the coupling device of the sleeve can extend further in the proximal direction from a proximal end of the coupling piece of the shaft and, at their proximal end, each have at least one insertion bevel.

Corresponding engagement bodies present in the receiving bore of the handle can be inserted in turn into these continuations of the longitudinal grooves, in order for the handle to be secured against rotation with respect to the sleeve and therefore indirectly with respect to the actuation rod.

The distal end portion of the sleeve in which the longitudinal grooves extend can, for example, have a greater diameter than the rest, as a result of which, together with the insertion bevels, a "crown-shaped" coupling device is obtained which, because of the insertion bevels, can be inserted quickly and intuitively into the receiving bore of the handle.

These and further advantages are set forth in the following description with reference to the accompanying figures. The reference to the figures in the description is for assisting with the description and for simplified understanding of the subject matter. The figures are merely schematic depictions of illustrative embodiments of the invention.

DETAILED DESCRIPTION OF THE INVENTION

Figure 1:
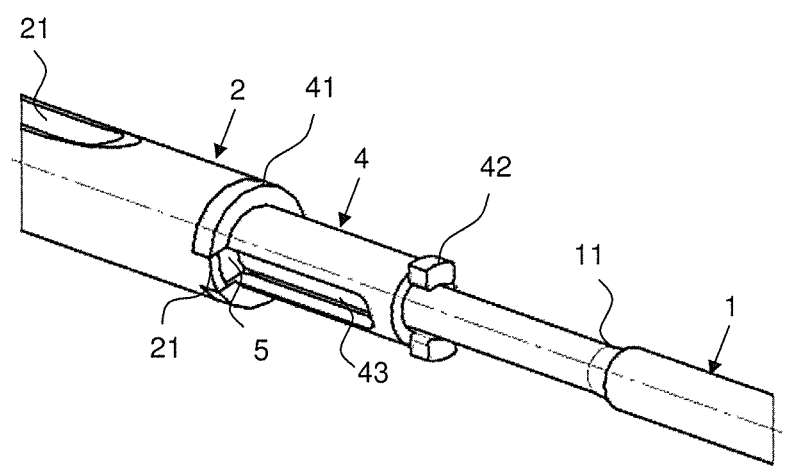
FIG. 1 shows a perspective partial view of the retractor, with the actuation rod in the distal end position of movement.
Figure 2:
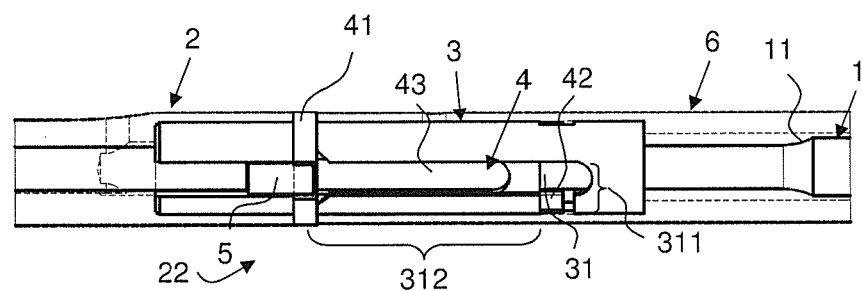
FIG. 2 shows a plan view of part of the retractor with transparent shaft in the actuation position of FIG. 1.

The perspective partial view of the retractor according to the invention in FIG. 1 shows a portion around the bayonet connection via which the retraction structure 20 (see FIGS. 9a and 9b) is coupled to the shaft 6 (see FIG. 2). The actuation rod 1 can be seen, which constitutes the actual transmission member from the handle to the retraction structure 20. The actuation rod 1 has a tapering 11, whereby the diameter of the actuation rod 1 in its proximal part (to the right in the figure) is larger than in its distal portion (to the left in the figure). It is thus possible to achieve a relatively space-saving tool head, while the torsional stiffness in the proximal portions is ensured.

The retraction structure 20 (not shown in the figure) is situated in an area lying to the left outside the depicted area, although the figure does show the shaft-shaped attachment portion 2 of the retraction structure 20 from which the bayonet element 4 extends in the proximal direction (to the right in the figure). The bayonet element 4 is welded to the attachment portion 2, and, to make production easier, the bayonet insert 4 has a collar 41 bearing on the proximal end of the attachment portion 2. The collar 41 has an interruption or cutting, in which a lug 21 of the attachment portion 2 engages in order to define a predetermined angle position during assembly. At the proximal end, the bayonet element 4 has two claws 42, which lie opposite each other, extend radially outward and can be brought into engagement with another bayonet element 3 (see FIG. 2). The "inner" bayonet element 4 assigned to the attachment portion 2 is referred to as the second bayonet element 4, and the "outer" bayonet element assigned to the shaft 6 is referred to as the first bayonet element 3 (see FIG. 2).

A cam 5 is guided on the actuation rod 1 for conjoint movement therewith and, in the depicted actuation position of the actuation rod 1, is received in a niche 23 (see FIG. 6) located between the lug 21 and the interruption of the collar 41 of the second bayonet element 4. In a movement of the actuation rod 1 in the proximal direction, the cam 5 is entrained out of the niche 23 and travels along the longitudinal slit 43, which is present in the wall of the second bayonet element 4 (see FIG. 3 to FIG. 7).

The part of the retractor depicted in FIG. 1 is shown in a plan view in FIG. 2, where the actuation rod 1 and therefore also the cam 5 are located in the same distal end position of movement as in FIG. 1. Here, however, the shaft 6 and the attachment portion 2 of the retraction structure are shown as transparent, such that the guiding of the bayonet elements 3, 4 one into the other can be seen. From the collar 41 of the second bayonet element 4, an insert portion extends in the distal direction (to the left in the figure), with which insertion portion the second bayonet element 4 is guided in the attachment portion. The longitudinal slit 43 extends in the distal direction both through the collar and also through the insertion portion. The first bayonet element 3 has an L-shaped slit 31, which has a longitudinal axial portion 312 and a circumferential portion 311. The slit 31 has a width dimensioned such that the claws 42 of the second bayonet element 4 and also the cam 5 can be received therein. The first bayonet element 3 is connected to the shaft 6 for conjoint rotation therewith and, together with the second bayonet element, forms the bayonet connection for coupling the shaft 6 to the attachment portion of the retraction structure.

Figure 3:
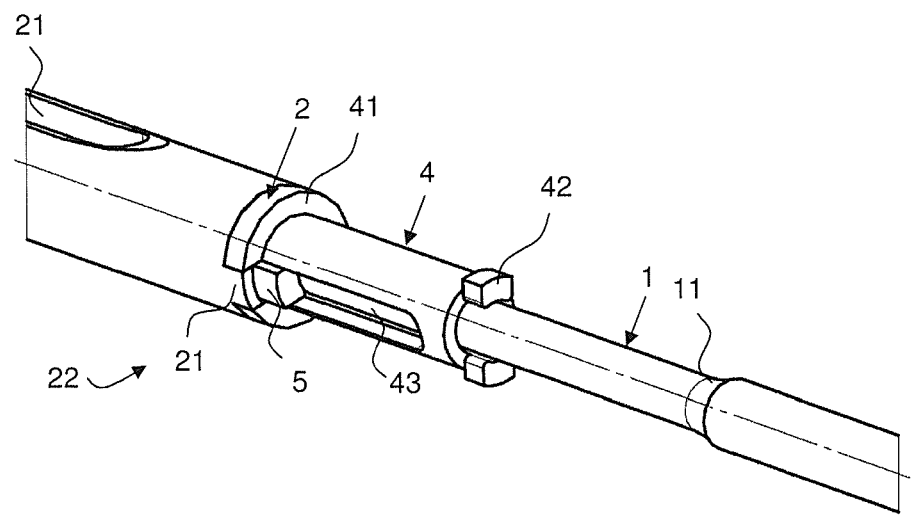
FIG. 3 shows a perspective partial view of the retractor, with the actuation rod in a distal working position.
Figure 4:
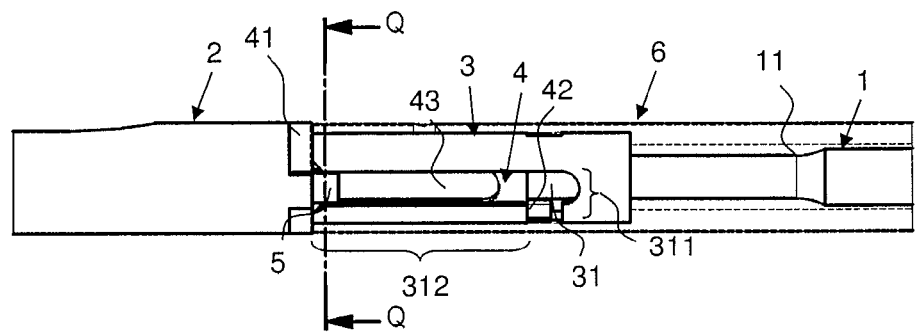
FIG. 4 shows a plan view of part of the retractor with transparent shaft in the actuation position of FIG. 3.

FIG. 3 and FIG. 4 show a perspective view and a plan view, respectively, of the portion of the retractor around the bayonet connection, wherein the actuation rod 1 has been moved a slight distance in the proximal direction; it is no longer located in the distal end position of movement but in a working position. In this position, the cam 5 is no longer completely received in the niche 23 (see FIG. 6) and instead emerges a distance therefrom. The radial extent of the cam 5 is dimensioned such that it not only extends through the second (inner) bayonet element 4 but also engages in the longitudinal axial portion 312 of the slit 31 of the first bayonet element 3, thereby securing the two bayonet elements 3, 4 against rotation relative to each other.

Figure 5A:
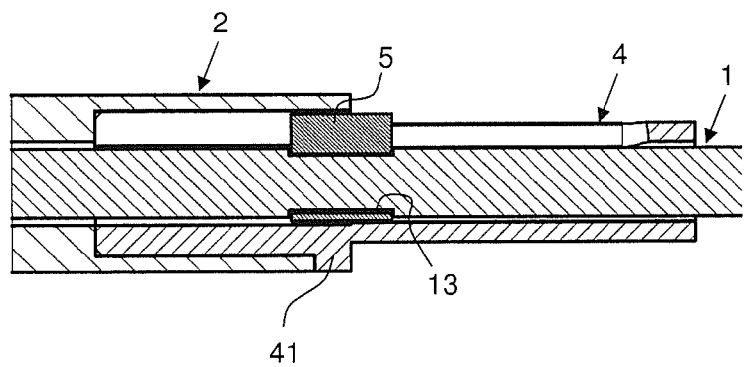
FIG. 5a shows a longitudinal sectional view of part of the retractor without bayonet sleeve and shaft, in the actuation position of FIG. 3.
Figure 5B:
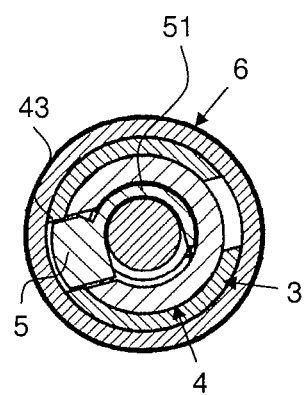
FIG. 5b shows a cross-sectional view of the shaft of the retractor.

FIG. 5a shows a section of the retractor with respect to the central longitudinal plane, with the shaft 6 cut away. The connection of the cam 5 to the actuation rod 1 can be clearly seen here. The actuation rod 1 has a circumferential recess 13, onto which the cam 5 is fitted with a foot. The foot 51 is C-shaped, as is shown in the cross-sectional view in FIG. 5b, where the sectional plane Q from FIG. 4 is represented. The thickness of the C-shaped foot 51 corresponds at most to the depth of the recess 13.

Figure 6:
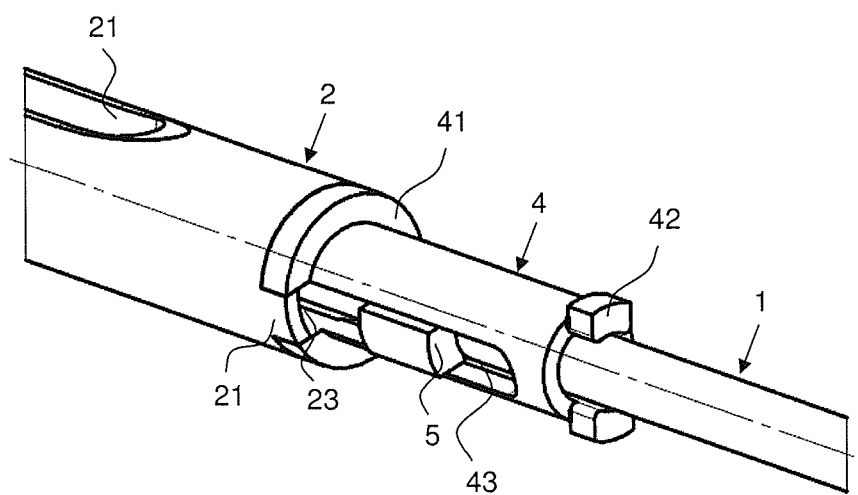
FIG. 6 shows a perspective partial view of the retractor, with the actuation rod in a central working position.
Figure 7:
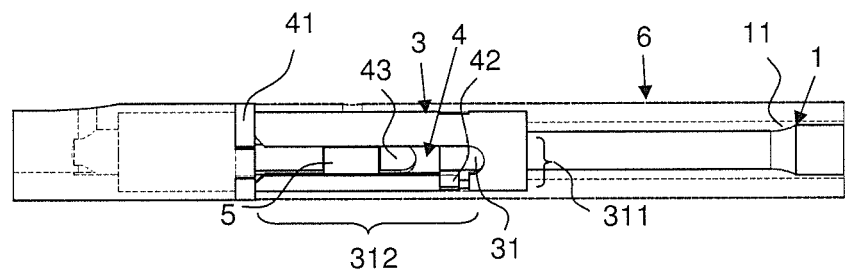
FIG. 7 shows a plan view of part of the retractor with transparent shaft in the actuation position of FIG. 6.

FIG. 6 and FIG. 7 each show a perspective partial view of the portion around the bayonet connection, as has already been shown in FIG. 1 to FIG. 4.

The actuation rod 1 is located in a central working position, wherein the cam 5 has here come completely out of the niche 23 and can exert its locking function, since it simultaneously engages in the first (outer) bayonet element 3 and the second (inner) bayonet element 4.

Figure 9A:
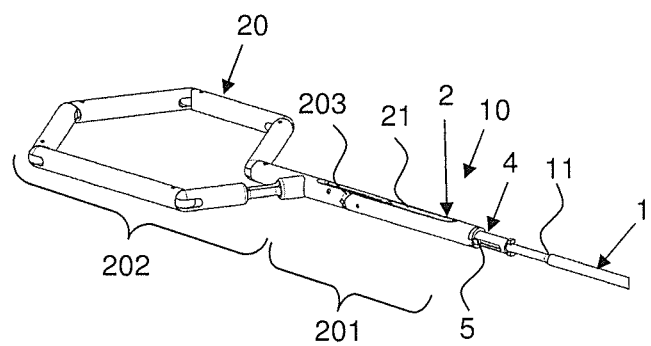
FIGS. 9a and 9b show perspective views of the distal end of the retractor with closed retraction structure.
Figure 9B:
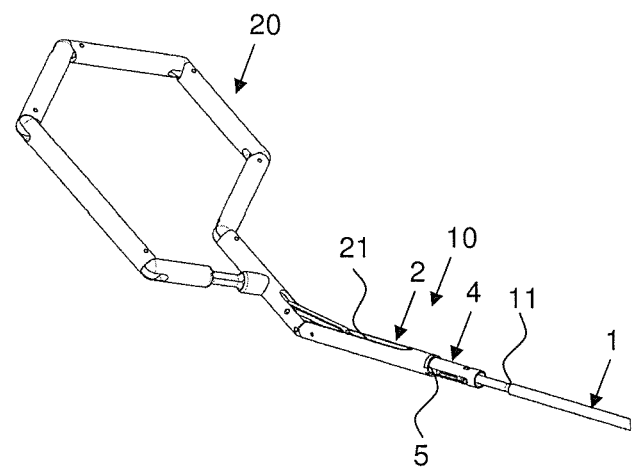
Figure 10:
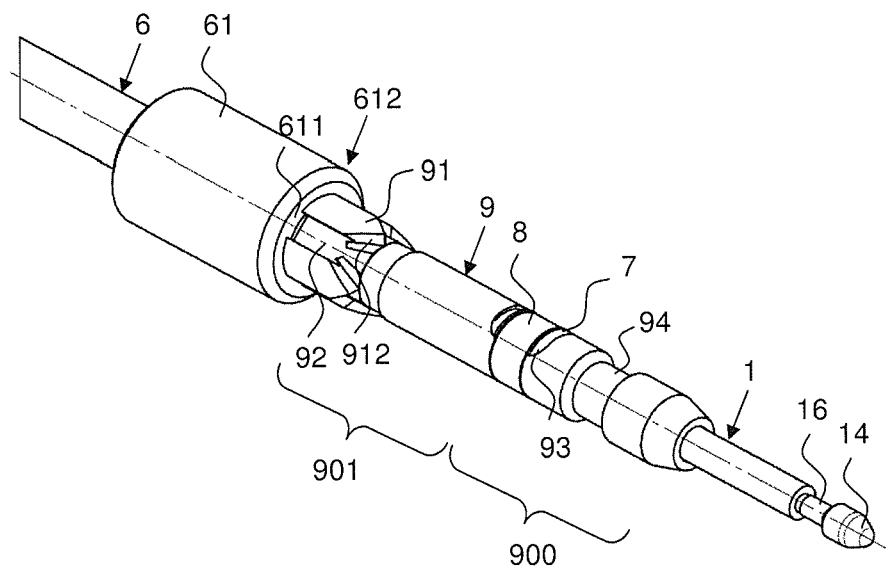
FIG. 10 shows a perspective partial view of the proximal end of the retractor with the handle cut away.
Figure 11:
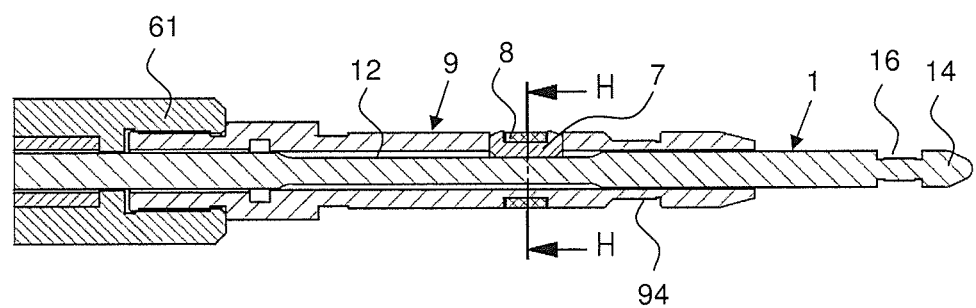
FIG. 11 shows a longitudinal section of the view shown in FIG. 10, FIGS. 12a and 12b show cross-sectional views of the proximal end of the retractor with the handle cut away.

In the positions of movement of the actuation rod 1 and of the cam 5 shown in FIG. 1 and FIG. 2, the bayonet connection could be accidentally opened, since the cam 5 does not yet engage with a locking action in the two longitudinal slits 312, 43 of the first bayonet element 4 and second bayonet element 3. The proximal end of the retractor 10, with coupled retraction structure 20, is shown in FIG. 9a and FIG. 9b, the actuation rod 1 in FIG. 9a being located in the position of movement of FIG. 1, and the actuation rod 1 in FIG. 9b being located in the position of movement of FIG. 3. The actuation rod 1 is here articulated on a linking rod or transmission arm, which is connected eccentrically to a force introduction point of the pivotable distal part 202 of the retraction structure 20, while the attachment portion 2 forms the stationary part 201 of the retraction structure 20. The pivotable part 202 and the stationary part 201 are connected via the joint 203, of which the joint axis forms the pivot axis of the two parts 201, 202 of the retraction structure 20. In the position of extension of the retraction structure 20, the linking rod or transmission arm is received in a slit 21, such that the retractor 10 in this position can be safely inserted into the body.

Figure 8:
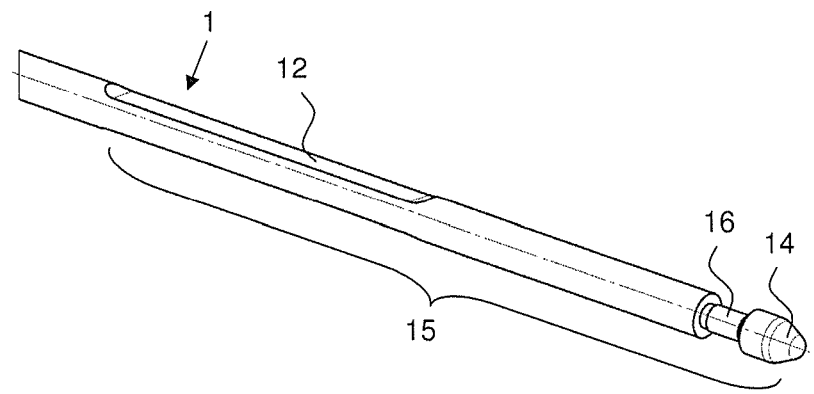
FIG. 8 shows a perspective view of the proximal end portion of the actuation rod.

In order also to prevent accidental opening of the bayonet connection in the position of extension, it is proposed according to the invention to provide an anti-rotation means located near the handle and acting with a form fit on the flattened part 12 of the actuation rod 1, said flattened part 12 being present in the proximal end portion 15 of the actuation rod, as is shown in FIG. 8. The proximal end portion 15 of the actuation rod 1 is intended to be inserted into the handle 10 (see FIGS. 13a and 13b). The actuation forces applied to the actuation device 101 (see FIGS. 13a and 13b) are applied to the mushroom-shaped head 14, in the case of pressure forces, and to the throat 16, in the case of tensile forces, while the actuation rod 1 is held secure against rotation with respect to the handle 10 via the flattened part 12, which is brought into engagement with a clamping block arranged in a fixed position on the handle 10.

This anti-rotation means located near the handle is shown in FIG. 10 to FIG. 12b. For this purpose, the sleeve 9 is designed to be connected to the handle 10 (see FIGS. 13a and 13b) for conjoint rotation and movement therewith.

To lock the axial movement of the sleeve 9 with respect to the handle, the sleeve 9 has a circumferential groove 94 that can be brought into engagement with one or more corresponding engagement means of the handle, while, in order to secure the degree of freedom in rotation, the grooves 92 extending along the longitudinal axis are provided in the distal end portion 901 of the sleeve 9. The grooves 92 are arranged in a head area, of which the diameter is greater than the diameter of the sleeve 9 in the remaining areas. The longitudinal grooves 92 are distributed at uniform angular intervals about the circumference, wherein the webs 91 between the individual grooves 92 are beveled in order in each case to form an insertion bevel 912. The insertion bevels 912 make it easier to bring the sleeve 9 into engagement with the handle, since the insertion bevels 912, when brought into contact with the corresponding engagement ribs of the handle, turn these automatically to the angle position suitable for the coupling. The shaft 6 is connected releasably to the sleeve 9, the angle being established using the same grooves 92 that are also used for the rotationally fixed coupling to the handle. At its proximal end, the shaft 6 has a coupling piece 61 which, at its proximal end, has inwardly protruding tongues 611, which in each case engage with a locking action in one of the grooves 92 on the "head" of the sleeve, said grooves extending further in the distal direction under the coupling piece 61.

The actuation rod 1 is guided in the sleeve 9, with the flattened part 12 lying in the area under the opening 93. A clamping block 7, of which the inner face is plane and which bears on the flattened part 12 of the actuation rod 1, is inserted into the opening 93. A pressing device 8, in this case a rubber band, is guided circumferentially around the sleeve 9 and the clamping block 7. The pressing device 8 exerts a radially inwardly directed force on the clamping block 7, as a result of which the latter is pressed onto the flattened part 12 and, even in the state when not coupled to the handle, is received in a manner secure against loss in the opening 93. In the state when inserted into the handle, the sleeve 9 or the clamping block 7 has only very little radial play in the corresponding receiving bore of the handle, as a result of which, even when the actuation rod 1 is subjected to a torque, the clamping block 7 cannot be pressed radially outward, and instead its flanks bear with a locking action on the side faces of the opening 93 of the sleeve 9.

Figure 12A:
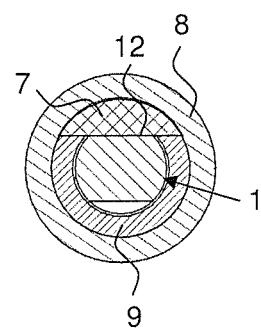
Figure 12B:
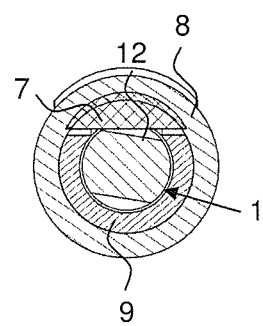

FIG. 12a and FIG. 12b show the cross section according to the section plane H (see FIG. 11), wherein the clamping block 7 is shown in its locking state in FIG. 12a and in its release state in FIG. 12b. To ensure that the actuation rod 1 can be separated from the sleeve 9, the latter already has to be uncoupled from the handle, since the clamping block 7 cannot otherwise perform a radial movement. In order to remove the actuation rod 1 from the sleeve 9, the latter has to be rotated about its longitudinal axis, as a result of which the clamping block 7 is moved radially outward and the engagement with the flattened part 12 is canceled. As a result, the actuation rod 1 can be withdrawn from the sleeve 9. For assembly, the actuation rod 1 first has to be inserted into the sleeve 9 and optionally turned until the clamping block 7 bears with its inner face on the flattened part 12 of the actuation rod 1, such that the clamping block is received so far radially inward into the opening that its outer contour is flush with the outer contour of the sleeve 9.

Figure 13A:
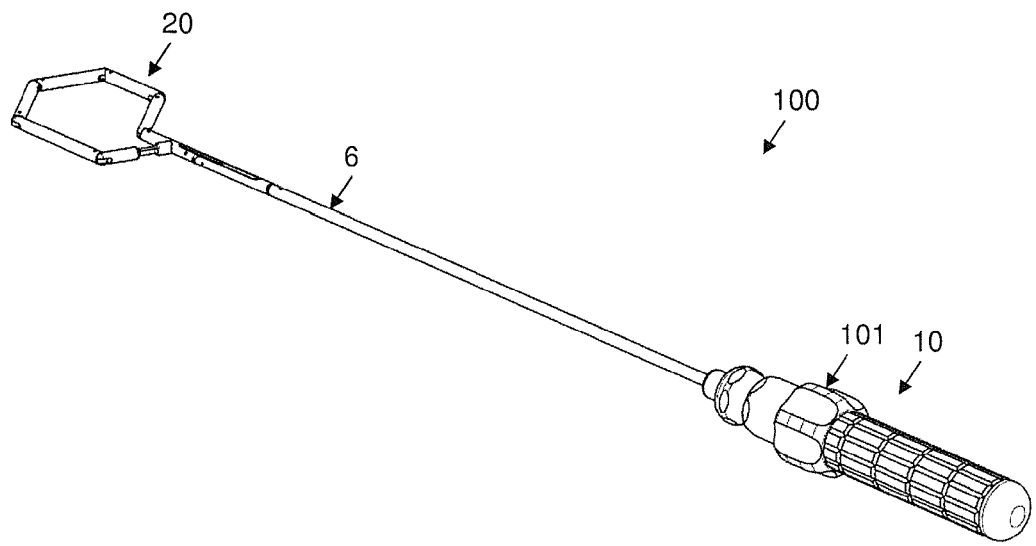
FIG. 13a shows a perspective view of the retractor with the actuation rod in the distal end position of movement.
Figure 13B:
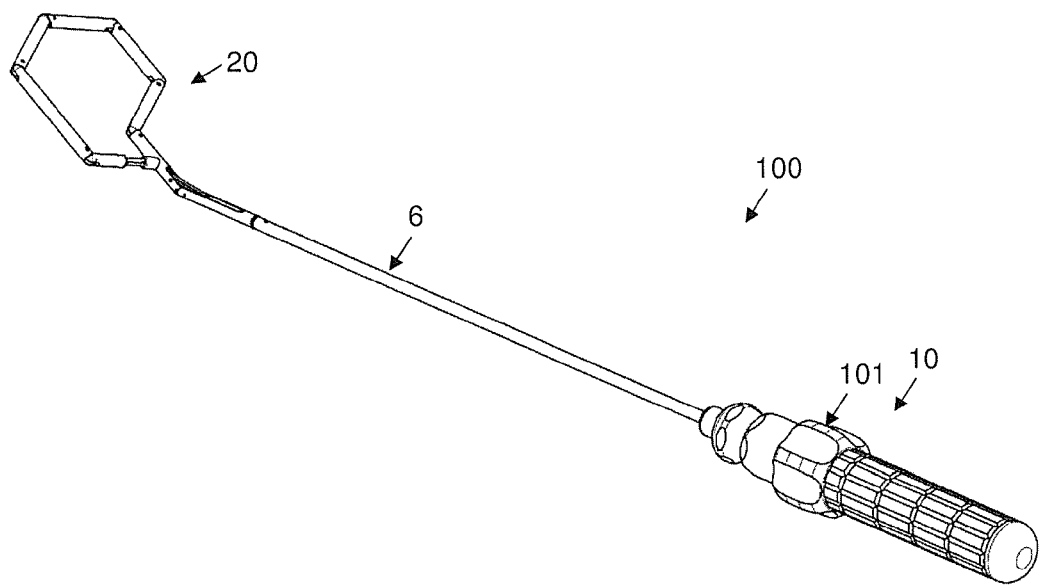
FIG. 13b shows a perspective view of the retractor with the actuation rod in a central working position.

The assembled retractor 100 is shown in FIG. 13a and FIG. 13b. In the extended state in FIG. 13a, only the anti-rotation means near the handle is engaged and prevents the bayonet connection from being accidentally opened, whereas, in the pivoted state in FIG. 13b, the engagement of the cam 5 in the two longitudinal slits 312, 43 of the bayonet elements 3, 4 also contributes to securing the bayonet connection against rotation. The actuation element 101 of the handle 10 is designed here as a rotary wheel 101 and is operatively coupled to the actuation rod in order to generate a pivoting movement of the retraction structure 20.

The invention claimed is:

1. An assembly method for a microsurgical instrument, which has a proximal handle mechanically connected to a hollow shaft, which shaft is coupled releasably to a tool head via a bayonet connection, wherein the handle has at least one actuation device, which is operatively coupled to an actuation rod that is guided in the shaft, wherein the bayonet connection has a first bayonet element and a second bayonet element with respective longitudinal slits which are aligned in a locked state of the bayonet connection, and at least one longitudinally movable cam is guided axially in the longitudinal slits, and wherein the actuation rod is inserted with its proximal end portion into the handle and has at least one flattened part, which is engaged by at least one clamping block arranged on the handle in a fixed position with respect to a longitudinal axis, said method comprising the steps of:
   a) making available the handle, the hollow shaft and the tool head, with the actuation rod operatively coupled thereon;
   b) pushing the shaft, with the first bayonet element at a front, over the actuation rod and bringing the first bayonet element of the shaft into engagement with the second bayonet element;
   c) rotating the shaft and the tool head relative to each other until the bayonet connection is in the locked state, thereby also aligning the respective longitudinal slits of the first bayonet element and the second bayonet element;
   d) inserting the proximal end portion of the actuation rod into the handle, thereby engaging the flattened part of the actuation rod with the clamping block of the handle and securing the actuation rod against rotation relative to the handle;
   e) mechanically connecting the handle to the shaft; and
   f) moving the cam into the longitudinal slits and forming an anti-rotation means near the tool.

2. The assembly method according to claim 1, wherein the cam is connected to the actuation rod for conjoint movement therewith and, in step f), the actuation device of the handle is actuated and, in this way, the actuation rod is moved along the longitudinal axis and the cam is necessarily carried along with it.

3. The assembly method according to claim 1, wherein the respective longitudinal slits of the first bayonet element and the second bayonet element and at least one engagement body of the bayonet connection are at an angular offset in a release state of the bayonet connection, and wherein, in step b), a distal end of a bayonet element assigned to the shaft is brought to bear on the cam, and the cam is carried along in the movement of the shaft.

4. The assembly method according to claim 1, wherein, at a proximal end of the tool head, an attachment portion is present which has a niche that corresponds to a size and position of the cam, and wherein, before step c), step b) is carried out, i.e. moving the cam to a distal end position of movement, there receiving the cam in the niche and thereby releasing a degree of freedom of rotation of the first bayonet element and the second bayonet element.

5. The assembly method according to claim 1, wherein the tool head is a ring retractor, preferably a pivotable ring retractor.

6. The assembly method according to claim 1, wherein the microsurgical instrument has a sleeve which is connected in a rotationally fixed manner to the handle, in which the actuation rod is guided movably along the longitudinal axis, and wherein the sleeve has, in its wall, at least one opening in which the clamping block is fitted, and wherein, before step d), step c) is carried out, i.e. pushing the actuation rod into the sleeve until the flattened part is present at a longitudinal axis position of the clamping block, turning the actuation rod until the clamping block bears on the flattened part, and, together with the actuation rod, inserting the sleeve into the handle.

* * * * *